United States Patent [19]

Michaels, Jr.

[11] Patent Number: 5,685,846
[45] Date of Patent: Nov. 11, 1997

[54] DUAL CHAMBER INTERNAL BY-PASS SYRINGE ASSEMBLY

[75] Inventor: Thomas M. Michaels, Jr., Upper Saddle River, N.J.

[73] Assignee: Schott Parenta Systems, Inc., Montvale, N.J.

[21] Appl. No.: 394,712

[22] Filed: Feb. 27, 1995

[51] Int. Cl.⁶ .................................. A61M 37/00
[52] U.S. Cl. ................ 604/90; 604/181; 604/191; 604/82
[58] Field of Search ............... 604/89, 82, 85, 604/84, 90, 91, 181, 191, 218, 187, 219, 221, 222, 225, 230, 231

[56] References Cited

U.S. PATENT DOCUMENTS

| | | | |
|---|---|---|---|
| 4,613,326 | 9/1986 | Szwarc | 604/89 X |
| 4,952,208 | 8/1990 | Lix | 604/221 X |
| 5,122,117 | 6/1992 | Haba et al. | 604/90 |
| 5,429,610 | 7/1995 | Vaillancourt | 604/89 X |
| 5,472,422 | 12/1995 | Ljungquist | 604/89 |
| 5,489,266 | 2/1996 | Grimard | 604/89 |

*Primary Examiner*—Michael Powell Buiz
*Assistant Examiner*—N. Kent Gring
*Attorney, Agent, or Firm*—Eugene E. Renz, Jr., Esq.

[57] ABSTRACT

A syringe device for use with two components to be combined prior to discharge, comprising a syringe body without the proximal end, a syringe plunger rod threadedly engageable into a plunger and a lined seal for engagement with a needle hub. The syringe body has at the distal end a radially inwardly directed internal sealing ring dividing the body to define a distal chamber and a proximal chamber. Also provided is an internal bypass stopper sized to fit the syringe body and engage the sealing ring to sealingly separate the distal chamber and the proximal chamber. The stopper has a plurality of projections circumferentially spaced thereon for engagement with the syringe body on at least one side of the sealing ring. The projections define by-pass channels therebetween to permit flow of liquid from the proximal chamber to the distal chamber upon movement of the stopper toward the distal end.

10 Claims, 5 Drawing Sheets

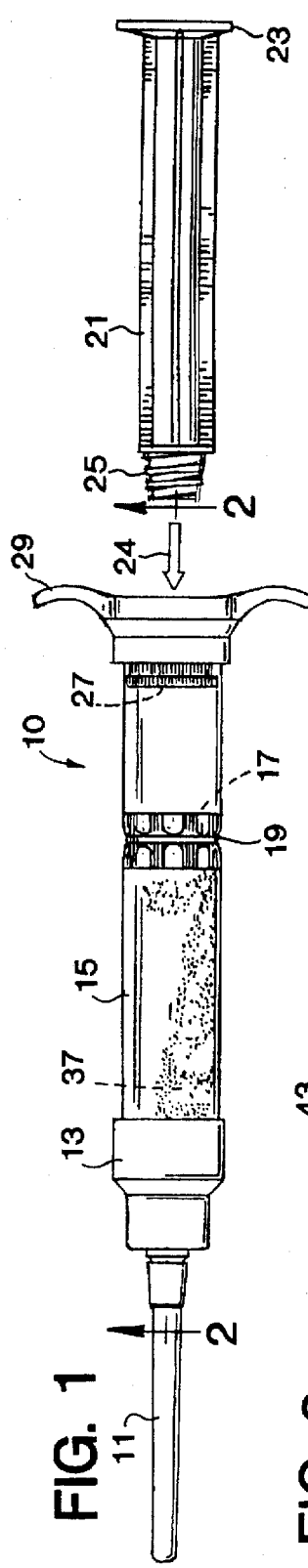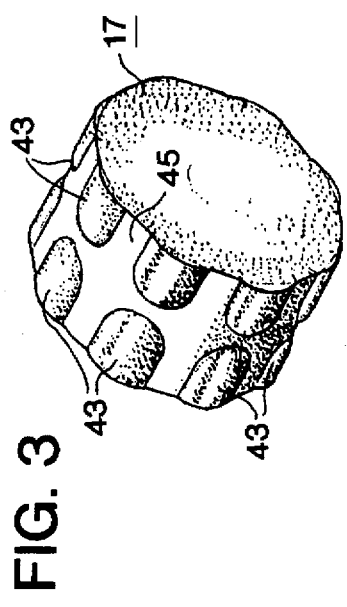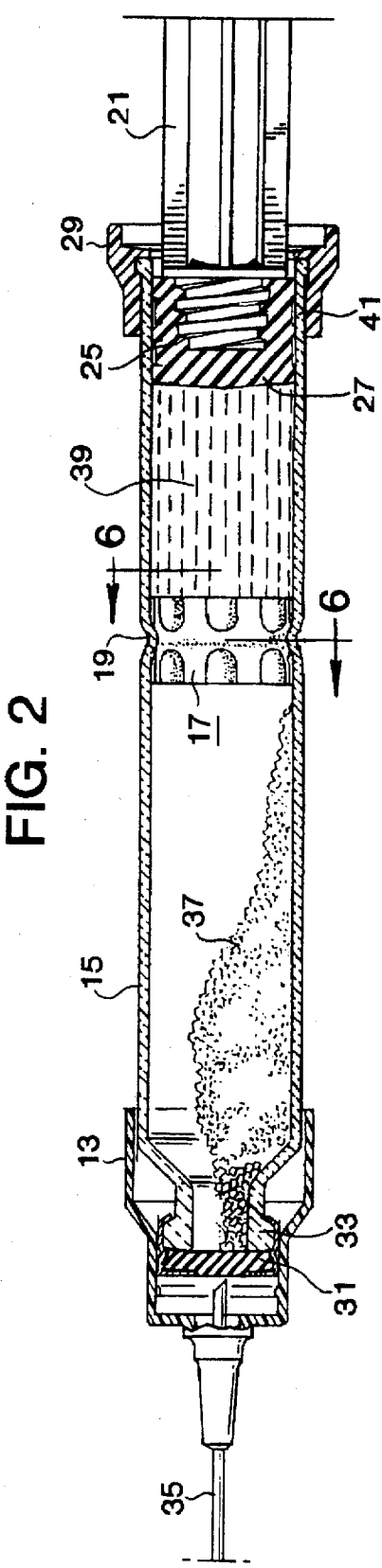
FIG. 1
FIG. 3
FIG. 2

DUAL CHAMBER INTERNAL BY-PASS SYRINGE ASSEMBLY

FIELD OF THE INVENTION

This invention relates to a dual chamber internal syringe assembly. More particularly, the invention relates to an internal by-pass syringe assembly which permits two liquids or a solid and a liquid to be packaged together in the same container and to be maintained separate from each other until time for mixing and use.

BACKGROUND OF THE INVENTION

The use of a syringe to administer medicaments to patients has long been recognized as an effective method of treatment. In some instances, where the medicaments are in powder form and need to be reconstituted by the addition of disfilled water or other liquids, administration of the medicament involves a number of steps and multiple uses of the syringe. When two medicines are to be mixed prior to administration, often times this procedure involves (i) insertion of a syringe into a first container, (ii) withdrawal of the contents and then (iii) withdrawal of the syringe, (iv) insertion of the syringe into a second container, (v) discharge of the first contents into the second container, (vi) mixing the two components thoroughly, and (vii) withdrawing the admixed contents, finally followed by (viii) administration of the medicament to the patient. It would be a great advantage to the art if many of these steps could be combined or avoided altogether.

Some methods have been proposed to avoid the above described difficulties through the use of what are known as dual chamber syringes with an external by-pass. Several of these are manufactured for use in packaging drugs. The drugs typically are liquid contained in both the syringe chambers, with the two liquids being mixed prior to administration. In addition, several manufactures have used these dual chamber syringes for packaging lyophilized drugs that axe sublimated in the syringe. Again, the dual chamber designs use an external by-pass which causes certain mixing and surging problems. Some quantity of drugs can remain in the external by-pass and potentially can contaminate exposed areas of the syringe. In instances where the medicament is toxic or corrosive, the preparer and user of the syringe is put at an undesirable risk. Another disadvantage of the external by-pass is the fact that the by-pass protrusion prevents affixing labels to the outside of the barrel.

A different design employs the use of vents to permit passive mixing of a liquid and a solid in one chamber of the syringe. This design employs a central by-pass stopper which is designed to create turbulence upon breaking loose of the stopper and activation of the stopper to thereby enhance mixing of the materials in the tube chambers.

Another internal stopper design is used in dual compartment vials held in place by a constriction in the body of the vial. In this instance, the stopper serves as a barrier and is dislodged after activation to permit the two materials in the dual compartments to co-mingle and combine. In another embodiment of the prior art, a syringe has been manufactured that is, in fact, a combination syringe and vial. The stopper closing the vial is held in place by a constriction and is vented to permit introduction of a liquid into the vial portion. The stopper then serves as a plunger when the contents of the syringe are expelled.

Other attempts to achieve an adequate design have used modifications of the plunger rod in conjunction with a syringe. The syringe is activated by threading the plunger rod toward the proximal end which breaks the by-pass stopper loose and moves it slowly past the external by-pass. The plunger rod only moves freely as in a traditional syringe after the last male thread on the plunger rod passes the last female thread in the finger grip.

Accordingly, it would be a great advance in the art if a simple, effective dual chamber syringe could be provided which would overcome the deficiencies of those designs presently known in the industry.

It is an object of this invention to provide a simple, direct dual compartment syringe with an internal by-pass mechanism.

Another object of the present invention is to provide a dual compartment syringe which serves to mix the contents of the two chambers slowly and thoroughly, avoiding turbulence.

Yet another object is to provide a dual compartment syringe which avoids a surge or spurt of liquid in the distal chamber when the stopper breaks loose from its normal sealed condition and avoiding diluent being trapped in the external by-pass or between the central stopper and the plunger, which can be ejected backwards onto the hands of the operator.

Other objects will appear hereinafter.

SUMMARY OF THE INVENTION

It has now been discovered that the above and other objects of the present invention may be accomplished in the following manner. Specifically, an improved syringe device for use with two components to be combined prior to discharge has been discovered. The syringe device includes a syringe body, a syringe plunger rod threadedly engaged in to a plunger and at a distal end a lined seal for engagement with a needle hub.

A radially inwardly directed internal sealing ring is provided in the middle of the body to define a distal chamber and a proximal chamber.

An internal by-pass stopper is sized to fit the syringe body and engage the sealing ring to sealingly separate the distal chamber and the proximal chamber. The stopper preferable has a plurality of projections spaced on at least one side of the stopper for engagement with the syringe body on at least one side of the sealing ring. The projections define by-pass channels therebetween to permit flow of liquid from the proximal chamber to the distal chamber upon movement of the stopper toward the distal end.

A plunger is fitted onto the plunger rod so that movement of the plunger toward the distal end causes fluid in the proximal chamber to displace the by-pass stopper and cause gentle flow of the liquid through the by-pass channels on the by-pass stopper to mix with either solids or liquids contained in the distal chamber. By the time the plunger reaches the by-pass stopper, all of the liquid has been forced past the by-pass stopper and the mixed syringe is ready for use to inject the medicament or other contents.

BRIEF DESCRIPTION OF THE DRAWINGS

These and other objects of the present invention and the various features and details of the operation and construction thereof are hereinafter more fully set forth with reference to the accompanying drawings, where:

FIG. 1 is a plan view of an internal by-pass syringe of the present invention, equipped with an attached, unarmed needle hub and needle shield and showing its associated plunger rod as detached from the syringe.

3

FIG. 2 is an enlarged, fragmentary sectional elevational view taken along the lines 2—2 of FIG. 1, showing details of construction and assembly of the internal by-pass syringe just prior to use.

FIG. 3 is an enlarged, isometric view of the internal by-pass stopper of this invention in a preferred embodiment.

Figure 4:
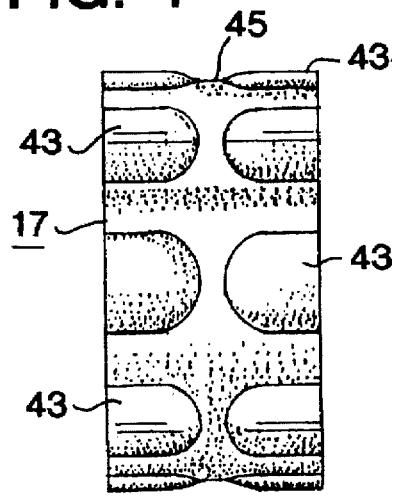

FIG. 4 is an enlarged, side elevational view of the by-pass stopper.

Figure 5:
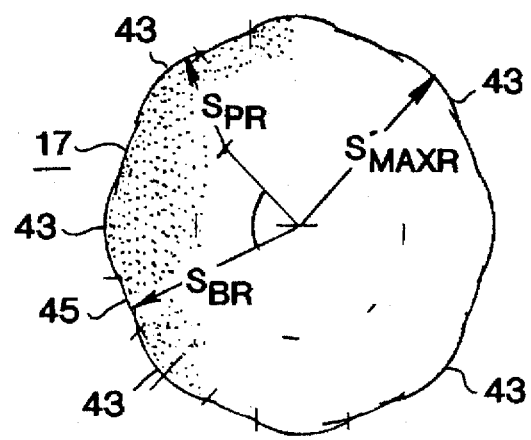

FIG. 5 is a right hand side elevational view of the by-pass stopper shown in FIG. 4.

Figure 6:
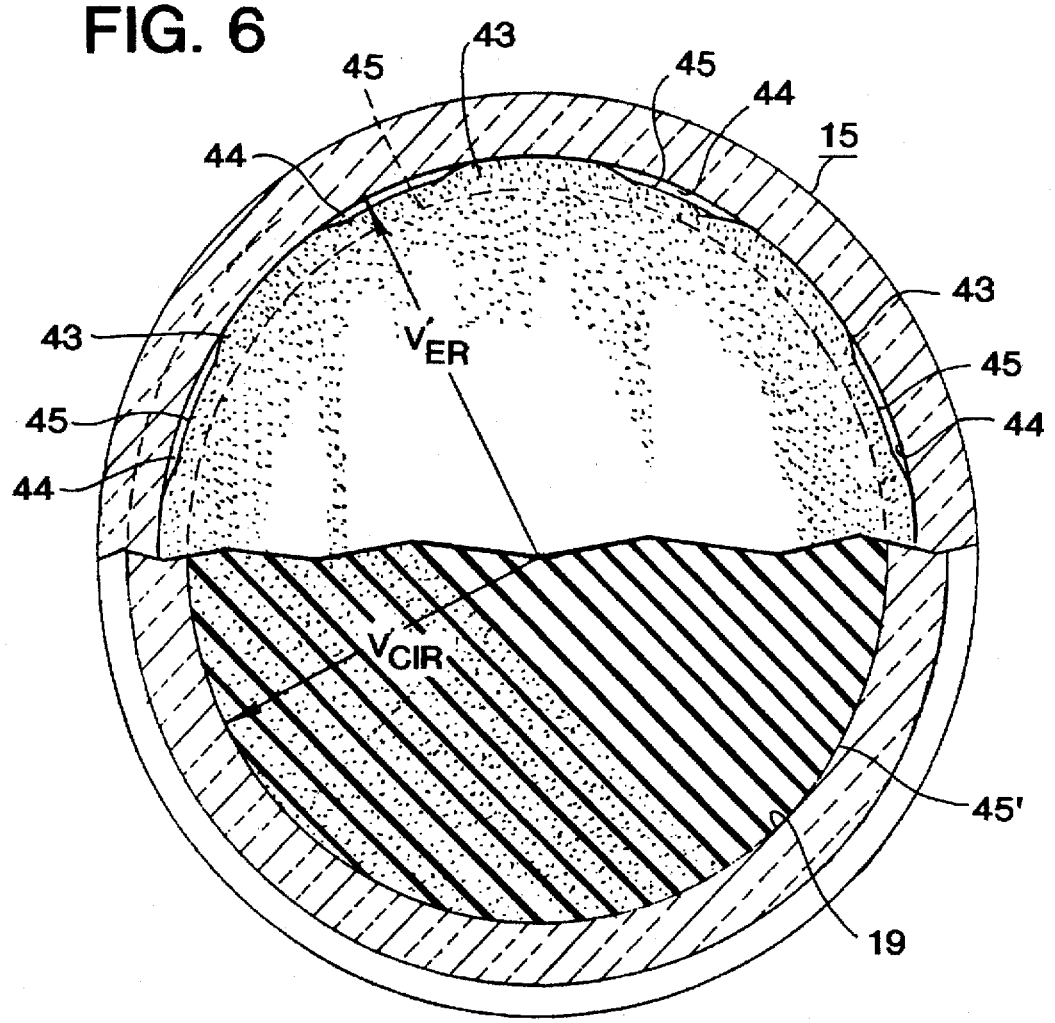

FIG. 6 is a greatly enlarged, stepped sectional view taken along the step line 6,6 of FIG. 2, showing details of the internal by-pass stopper as fitted at the internal sealing ring of the syringe body and also of the fitting of the internal by-pass stopper at the normal internal diameter of the syringe body.

FIGS. 7A–7E illustrates the sequential functions of the internal by-pass syringe of this invention in use.

Figure 8:
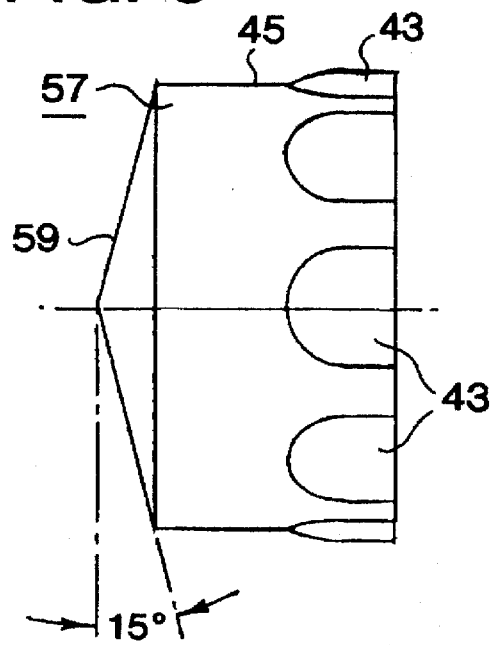

FIG. 8 is a side, elevational view of a modified or alternative embodiment of the by-pass stopper of this invention.

Figure 9:
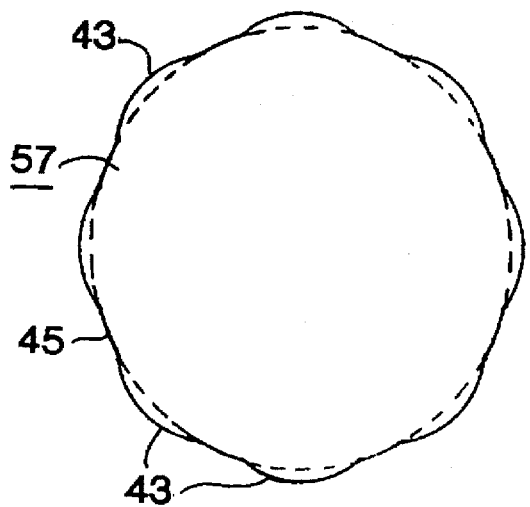

FIG. 9 is a right hand, elevational view of the by-pass stopper shown in FIG. 8.

Figure 10:
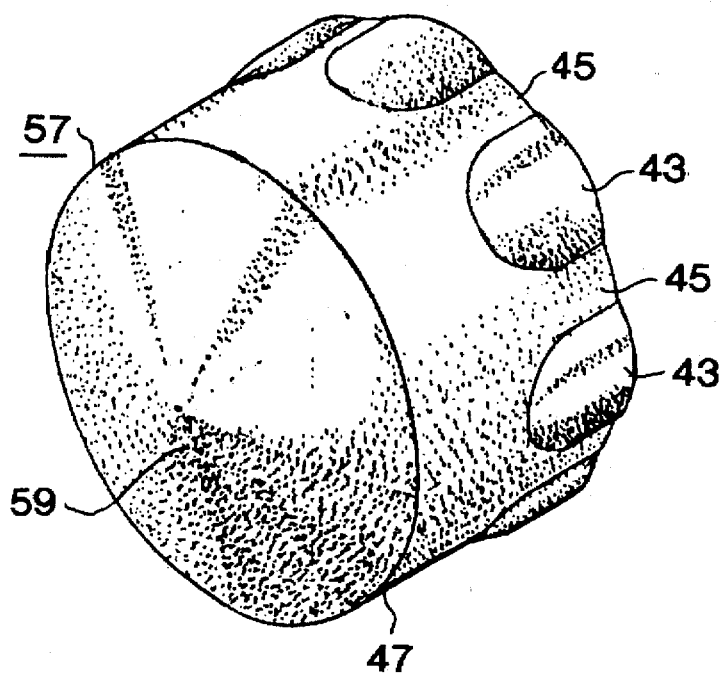

FIG. 10 is an enlarged, isometric view of the stopper shown in FIG. 8.

DETAILED DESCRIPTION OF THE PREFERRED EMBODIMENT

The syringe device of the present invention, shown generally by the reference number 10, provides for use of a two component medicament combination to be mixed prior to discharge. The elements of the syringe system 10 include a needle shield 11 which protects the needle itself and those using the device prior to the time when an injection is to be made. The needle is mounted to a needle hub 13 which in turn is mounted to a syringe body 15. Inside the syringe body 15 is an internal by-pass stopper 17, held in place by a radially inward internal sealing ring 19 formed in body 15. A plunger rod 21 is to be attached to the syringe for actuation by pressure on thumb rest 23 after the threads 25 have been threaded into plunger 27. This syringe is shown with a conventional syringe finger grip 29 for cooperative application of pressure on thumb rest 23 in the direction shown by the arrow 24 in FIG. 1.

Shown in FIG. 2 is an enlarged version of the device in FIG. 1 just prior to use. The plunger rod 21 has been attached to plunger 27 via threads 25. Lined seal 31 is shown mounted on the distal end 33 of the syringe body 15 and needle shield 11 has been removed to expose needle 35. At the appropriate time for use, needle 35 is moved toward the seal 31 to puncture it and provide access to the contents.

At this point, the powder 37 is separated from the liquid 39 by internal by-pass stopper 17 which is sealingly fitted into the radially inwardly directed internal sealing ring 19. Prior to use, the powdered contents 37 in the distal chamber are to be mixed with the liquid contents 39 in the proximal end 41 of the syringe body 15.

As can be seen in FIG. 3, equally spaced about the circumference of the internal by-pass stopper 17 are a series of outwardly directed, arcuately shaped projections 43 extending slightly above the circumferentially extending base circle 45 of the main body portion of the internal by-pass stopper 17. The arcuately shaped projections 43 extend inwardly a distance less than ⅓ the thickness of the by-pass stopper 17, from both end faces of the stopper,

4 leaving a centrally located, circumferentially extending band free of projections 43 and a base circle diameter 45 that is designed to engage with the sealing ring 19 of the glass syringe body 15 as shown in FIG. 2 of the drawings.

By-pass stopper 17 is shown enlarged in FIG. 3 where the projections 43 provide a raised portion and the remaining portion of the stopper 17 is a lower area 45 that is sized to engage the radially inwardly directed internal sealing ring 19. The relationship between the projections 43 and the sealing area 45 is illustrated in FIG. 4. FIG. 5, a side view of the stopper shown in FIG. 4, illustrates the by-pass stopper projection radius, $S_{maxr}$, the maximum radius of the stopper $S_{pr}$ and the base circle radius $S_{br}$. $S_{br}$ is, the radius of the sealing region 45 of stopper 17. FIG. 6 is a stepped, sectional view showing details of the stopper 17 and its relationship with the inner sealing ring 19 in the bottom half of FIG. 6 and with respect to the syringe body 15 in the top half of FIG. 6. The inner radius of the syringe body 15 $V_{ir}$ is greater than the by-pass sealing radius $S_{br}$ of the stopper 17 and the inner radius $V_{cir}$ of the sealing ring 19 of the syringe body 15 is smaller than the base circle radius $S_{br}$ of the by-pass stopper 17. When the by-pass stopper 17 is positioned as shown in FIG. 2 of the drawings, the sealing ring 19 of the syringe body 15 sealingly compresses the base circle 45 of radius $S_{br}$ of the by-pass stopper 17, forming a circumferentially extending sealing engagement between mid portion of the rubber by-pass stopper 17 and the sealing ring 19 of the syringe body 15 as indicated by 45 in FIG. 6 of the drawings. Also the max. radius $S_{pr}$ of the stopper 17 is slightly larger than the inner radius $V_{ir}$ of the syringe body 15 such that the apex of the projections 43 is only lightly compressed the plurality together forming a series of by-pass channels 44 between the inner surface of the syringe body 15 and the base circle 45 of the rubber stopper 17 and intermediate each of the projections 43 of the by-pass stopper 17.

Turning now to the series of Figures identified as FIGS. 7A through 7E, the sequential functioning of the internal bypass syringe of this invention is illustrated. Each of these illustrate progressive sequential movement of the syringe by-pass stopper 17 from the initial ready-to-use position shown in FIG. 2.

Figure 7A:
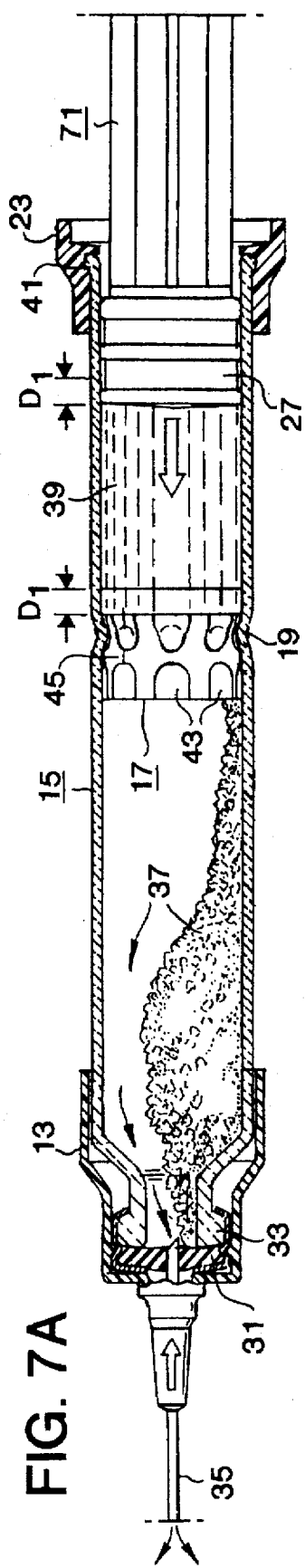
Figure 7B:
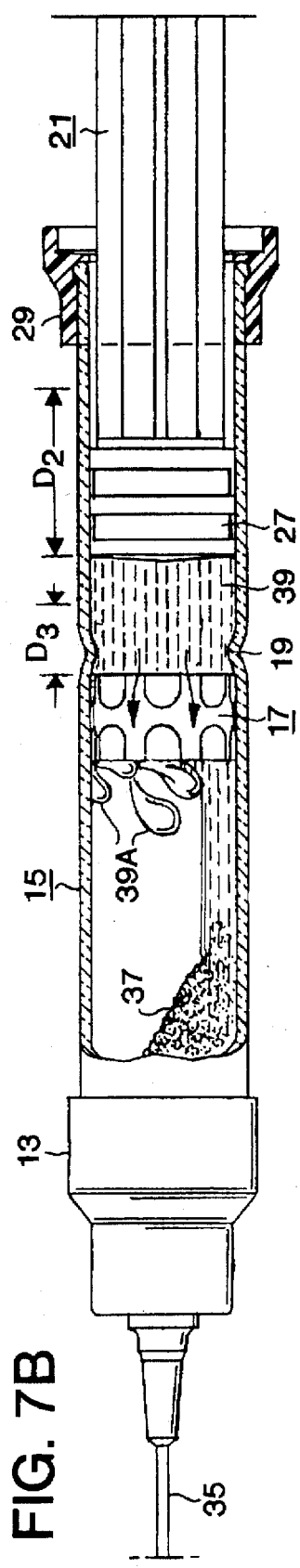

In FIG. 7A, the double ended needle and hub assembly 13 is moved proximally against the lined seal 31 as shown by the arrow, causing the needle to pierce the seal 31. In FIG. 7A, the plunger rod 21 moves plunger 27 a short distance D1 which compresses the liquid 39, causing the internal bypass stopper 17 to move a similar distance D1. This movement forces the bypass stopper 17 to disengage from the radially inwardly directed sealing ring 19 and causes projections 43 to deformably engage the sealing ring 19. At the same time, internal air flows in the direction shown by the arrows to vent. The plunger 27 then moves to the position shown in FIG. 7B, a distance D2, while stopper 17 has moved a distance D3 which is less than D2. Projections 43 engage the internal surface of syringe body 15. Fluid 39 is transferred by a non-turbulent or laminar flow and discrete drops 39A pass between projections 43 of stopper 17, dissolving the solid material 37 while the by-pass stopper 17 remains stationary.

Figure 7C:
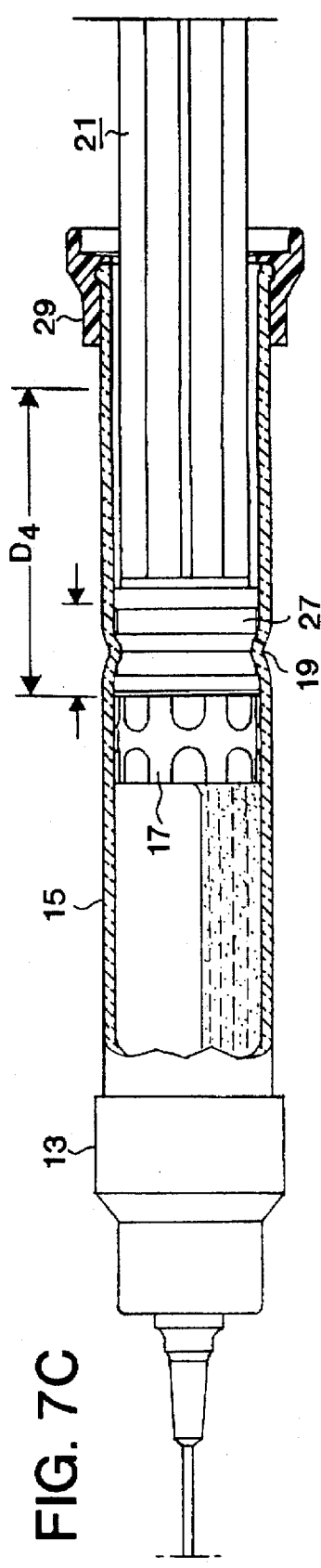
Figure 7D:
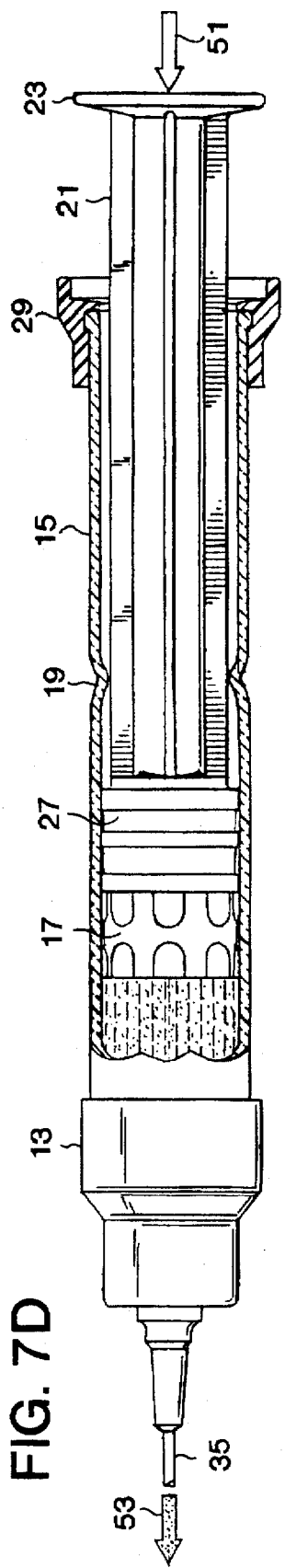

FIG. 7C illustrates the travel of the plunger 27 over a distance D4. All of the diluent is transferred around the stationary by-pass stopper 17 in a slow or non-turbulent flow, allowing mixing of the diluent and medicant and providing a large chamber for the visual examination of the mix before injection. When the by-pass stopper and plunger are in constant relative motion throughout the entire stroke leaving no large pre-injection visual inspection chamber, it is not possible to be sure that some of the diluent has not remained behind the by-pass stopper. Of course, if a liquid is contained in the distal end instead of a solid 37, mixing may be even easier. It is appropriate at this point to agitate the syringe to insure complete mixing.

After ensuring that all of the solids have been dissolved or are in solution, or that the two liquids are properly mixed, which can easily be determined by visual inspection, the contents are dispensed. This is accomplished by pressure on the thumb rest 23 in the direction shown by the arrow 51 which results in discharge of the mixed two component medication through needle 35 in the direction shown by arrow 53.

Figure 7E:
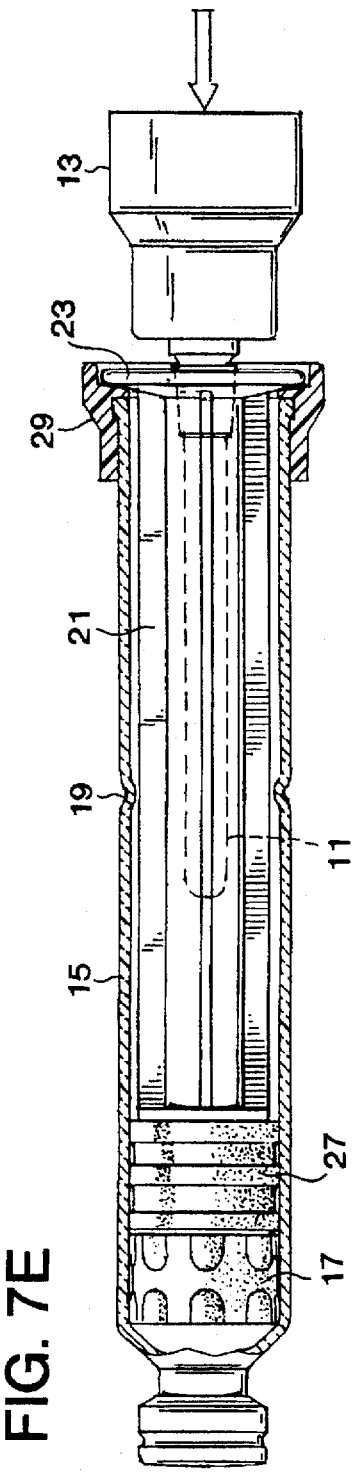

Finally, FIG. 7E represents the device of this invention in a final fully discharged condition.

An alternative embodiment is shown in FIGS. 8, 9 and 10 in which a second version of the internal bypass stopper 57 is shown. In this embodiment, the projections 43 at low area 45 are included only on the proximal end of the stopper 57. The distal end includes a cone shaped leading surface 59. As shown in FIG. 8, the angle of the cone with respect to a line perpendicular to the stopper axis is about 15°. Other angles are also effective. This stopper 57 is employed when a lyophilized product, such as solid 37, is so fine that it backfills into spaces between projections 43 on stopper 17. This fine powder coats everything on the inside of syringe 15 to give a frosted look to the by-pass stopper when it is stored during its shelf life. The projections have been removed from the distal end of stopper 57 to keep lyophilized powder out of the by-pass stopper and provide a better seal on the medicament side of the two component systems. The glass to rubber seal between low area 45 on stopper 57 is sufficient to prevent migration of extremely fine particles between the stopper and the glass.

The present invention has the advantage of having no surface protrusion on the syringe body and is thus much more adaptable for label affixing. In contrast, prior art external by-pass devices, make labeling much more difficult.

Various embodiments of the present invention have been described and illustrated herein. It is not intended to limit the invention and changes and modifications be made therein all within the scope of the following claims.

What is claimed is:

1. A syringe assembly comprising:

an elongated hollow tubular barrel having an inner peripheral surface and a discharge opening at one end and;

means defining a radially inwardly directed circumferentially extending rib in the inner peripheral surface of said barrel dividing said barrel into a first medicament chamber on one side of said rib and a second diluent chamber on the opposite side of said rib;

a by-pass stopper engageable interiorly of said barrel having a circumferentially extending exterior sealing surface of a predetermined diameter greater than the diameter of the rib to provide a seal between said chambers when engaged therewith and means defining at least one axially extending flow path on at least one side of said sealing surface providing fluid communication between said chambers when said stopper is displaced axially relative to the rib.

2. The syringe assembly of claim 1 wherein said bypass stopper includes projections circumferentially spaced on both sides of a central portion, said central portion circumferentially engaging said sealing rib.

3. The syringe assembly of claim 1 wherein said bypass stopper includes a plurality of projections circumferentially spaced thereon only on the diluent chamber side of the by-pass stopper.

4. The syringe assembly of claim 3 wherein said internal by-pass stopper includes a cone shaped end facing said first medicament.

5. The syringe assembly of claim 1 which further includes a needle hub assembly for mounting a needle on said device.

6. A method for dispensing two components to be combined prior to discharge using a syringe having a distal end and a proximal end, comprising the steps of:

placing a liquid in the proximal end of a syringe and a medicament mixable with said liquid in the distal end of said syringe, said syringe including a body having a radially inwardly directed internal sealing rib to define said distal and proximal chambers and a by-pass stopper having a portion sealingly separating said chambers, and a plurality of projections circumferentially spaced thereon on at least one side of said sealing portion defining by-pass channels;

moving said by-pass stopper axially to displace the sealing portion from the rib to permit flow of liquid through said by-pass channels from said proximal end to said distal end to form a dispensable combination of said liquid and said medicament; and dispensing said dispensable combination as desired.

7. The method of claim 6 wherein said by-pass stopper includes projections circumferentially spaced on both sides of a central portion, said central portion circumferentially engaging said sealing ring to provide a sealing engagement therebetween.

8. The method of claim 6 wherein said by-pass stopper includes a plurality of projections circumferentially spaced thereon only on the side of the by-pass stopper facing said distal end of the syringe.

9. The method of claim 6 wherein said internal by-pass stopper includes a cone shaped end facing said distal chamber.

10. The method of claim 6 which further includes a needle hub assembly for mounting a needle on said device.

* * * * *